United States Patent
Pebbles

[11] Patent Number: 5,900,291
[45] Date of Patent: May 4, 1999

[54] NON-LIGHT PENETRATING PHLEBOTOMY TUBE WITH TEMPERATURE SENSITIVE LEVEL INDICATOR

[76] Inventor: Patricia J. Pebbles, 52141 Quaker Hill La., Chesterfield Twp., Mich. 48051

[21] Appl. No.: 08/858,607
[22] Filed: May 19, 1997
[51] Int. Cl.⁶ .................................................. C09K 19/00
[52] U.S. Cl. ...................... 428/1; 06/571; 422/102; 422/913; 422/914; 422/915; 422/918; 428/34.1; 600/576; 600/584; 604/198; 604/263
[58] Field of Search .................. 428/1, 34.1; 422/102, 422/913, 914, 915, 918; 206/571; 600/576, 584; 604/263, 198

[56] References Cited

U.S. PATENT DOCUMENTS

| | | | |
|---|---|---|---|
| 4,774,838 | 10/1988 | Rickson | 73/295 |
| 5,086,780 | 2/1992 | Schmitt | 128/763 |
| 5,104,705 | 4/1992 | Quackenbush | 428/36.91 |
| 5,165,419 | 11/1992 | Sarstedt | 128/763 |
| 5,399,318 | 3/1995 | Mancilla et al. | 422/100 |
| 5,556,599 | 9/1996 | Ahmed | 600/576 |

OTHER PUBLICATIONS

The Fisher Catalog, B–D Microtainer Brand Amber Tube, p. 584, col. 2, 1991/92.

Primary Examiner—Nasser Ahmad
Attorney, Agent, or Firm—Joseph N. Breaux

[57] ABSTRACT

A non-light penetrating phlebotomy tube comprising a dark colored hollow tubular housing having an elongated cylindrical member wherein one distal end of the elongated cylindrical member is rounded and the other distal end of the elongated cylindrical member is open. A hermetic sealing member is received in the other distal end of the elongated cylindrical member for sealing the hollow tubular housing. The non-light penetrating phlebotomy further comprises a temperature sensitive level indicator coupled to the elongated cylindrical member for detecting the level of a fluid entering the dark colored hollow tubular housing.

2 Claims, 1 Drawing Sheet

NON-LIGHT PENETRATING PHLEBOTOMY TUBE WITH TEMPERATURE SENSITIVE LEVEL INDICATOR

TECHNICAL FIELD

The present invention relates to phlebotomy tubes and more particularly to a non-light penetrating phlebotomy tube for protecting the collected blood stored therein from light exposure. Moreover, the non-light penetrating phlebotomy tube is provided with a temperature sensitive level indicator for indicating to the phlebotomist technician the level of blood being collected thereby preventing overdrawing and underdrawing of the patient's blood.

BACKGROUND OF THE INVENTION

Phlebotomy tubes and phlebotomy tube holders for coupling thereto phlebotomy tubes used to collect a patient's blood sample are well known. Some such phlebotomy tubes and phlebotomy tube holders are described in U.S. Pat. Nos. 5,086,780, by Schmitt, 5,104,705, by Quackenbush, 5,165,419, by Sarstedt, and 5,399,318, by Mancilla et al. However, known drawing tubes (some having an anticoagulant composition, blood preservative, or the like stored therein) and phlebotomy tube holders are typically made of clear glass and/or plastic for enabling a phlebotomist technician to visual inspect the blood sample level collected and stored therein. During the drawing of the blood sample, it is critical that the phlebotomist technician can visually inspect the blood sample level to ensure that the minimum required amount of blood is obtained and that the blood is not overdrawn.

Some blood tests, such as, without limitation, vitamin deficiency tests, require that the blood sample not be exposed to light. Presently, for such blood tests, the technicians must immediately wrap the phlebotomy tube in aluminum foil or other material for preventing the blood sample from prolonged exposure to the light which is cumbersome and awkward. Nevertheless, such practices are often futile since even the slightest exposure to light can provide inaccurate blood test readings. Therefore, the blood sample must be discarded and redrawn.

It can be readily seen that there exists the continuing need for a non-light penetrating phlebotomy tube for protecting collected blood stored therein from light exposure; and, a non-light penetrating phlebotomy tube having a temperature sensitive level indicator for indicating to the phlebotomist technician the level of blood sample being collected thereby preventing overdrawing and underdrawing of the patient's blood.

SUMMARY OF THE INVENTION

The preferred embodiment of the non-light penetrating phlebotomy tube of the present invention solves the aforementioned problems in a straight forward and simple manner. What is provided is a non-light penetrating phlebotomy tube protecting the collected blood therein from light exposure. Moreover, the non-light penetrating phlebotomy tube is provided with a temperature sensitive level indicator for indicating to health care personnel the level of blood being collected thereby preventing overdrawing and underdrawing of the patient's blood.

The non-light penetrating phlebotomy tube comprises a dark colored hollow tubular housing having an elongated cylindrical member wherein one distal end of said elongated cylindrical member is rounded and the other distal end of said elongated cylindrical member is open; a hermetic sealing member received in said other distal end for sealing said hollow tubular housing; and a temperature sensitive level indicator coupled to said elongated cylindrical member for detecting the level of a fluid entering said dark colored hollow tubular housing.

In view of the above, an object of the invention is to provide a temperature sensitive level indicator which functions to change color as the warm blood is filled in the hollow tubular housing of the non-light penetrating phlebotomy tube.

Another object of the invention is to provide a non-light penetrating phlebotomy tube which may be supported by various types of phlebotomy tube holders used when drawing blood samples.

A further object of the invention is to provide a non-light penetrating phlebotomy tube which is useable with various types of needles.

In view of the above objects, a feature of the present invention is to provide a non-light penetrating phlebotomy tube which is simple to use and inexpensive to manufacture.

Another feature of the present invention is to provide a temperature sensitive level indicator which is a liquid crystal strip thermometer.

A further feature of the invention is to provide a temperature sensitive level indicator with self-adhesive material for adhering to the longitudinal surface of non-light penetrating phlebotomy tube.

The above and other objects and features of the present invention will become apparent from the drawings, the description given herein, and the appended claims.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

DESCRIPTION OF THE EXEMPLARY EMBODIMENT

Figure 1:
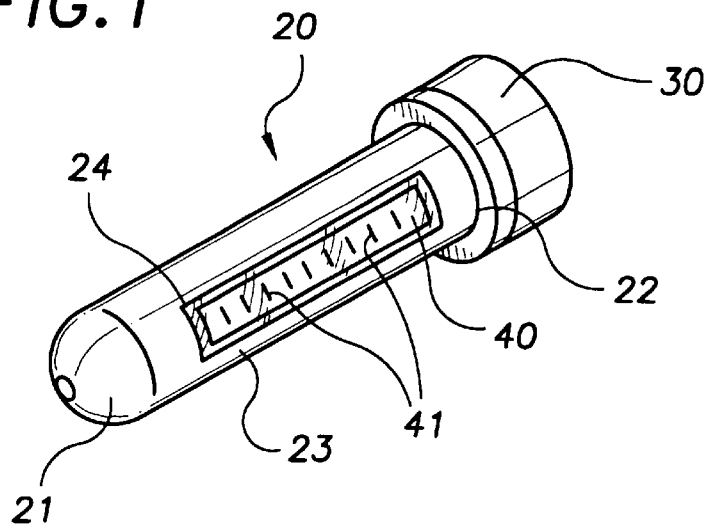
FIG. 1 illustrates a perspective view of the non-light penetrating phlebotomy tube and temperature sensitive level indicator of the present invention.
Figure 2:
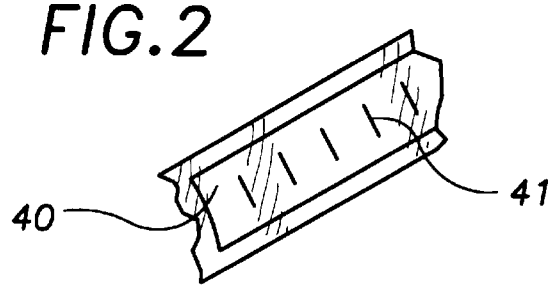
FIG. 2 illustrates a detailed view of the temperature sensitive level indicator of the embodiment of FIG. 1; and, FIG. 3 illustrates the non-light penetrating phlebotomy tube and temperature sensitive level indicator supported by a phlebotomy tube holder.

Referring now to the drawings, and in particular FIGS. 1–2, the non-light penetrating phlebotomy tube of the present invention is designated generally by the numeral 10. Non-light penetrating phlebotomy tube 10 is comprised of hollow tubular housing 20, hermetic sealing member 30, temperature sensitive level indicator 40.

Hollow tubular housing 20 is a hollow cylindrically shaped tube having a rounded end 21 and an elongated cylindrical member 23. Hollow tubular housing 20 is made of a dark colored glass. For example, any one of the following colors black, dark brown, dark purple or the like may be used wherein the density of such colored glass protects the blood from light exposure. Alternatively, a dark colored plastic may be used. Alternatively, the surfaces of hollow tubular housing 20 may be opaque. In the preferred embodiment, elongated cylindrical member 23 has formed therein rectangular surface area 24 extending a substantial portion of the length of elongated cylindrical member 23.

Open end 22 of hollow tubular housing 20 receives therein hermetic sealing member 30 for hermetically sealing hollow tubular housing 20. In the exemplary embodiment, hermetic sealing member 30 is made of silicone rubber.

Temperature sensitive level indicator 40 comprises thermally sensitive strip having a plurality of graduated marker indicators 41 for indicating to the phlebotomist technician the level of the blood rising in the hollow tubular housing 20. In the preferred embodiment, thermally sensitive strip is a liquid crystal strip thermometer having a back surface provided with a self-adhesive material for adhering the liquid crystal strip thermometer to the longitudinal surface of rectangular surface area 24. Temperature sensitive level indicator 40 functions to change color as the warm blood is filled in the hollow tubular housing 20. For example, temperature sensitive level indicator 40 may change to red or orange when a temperature of 90 to 100 degrees is detected.

Alternatively, temperature sensitive level indicator 40 instead of being self-adhesive may be integrated into the hollow tubular housing 20.

Figure 3:
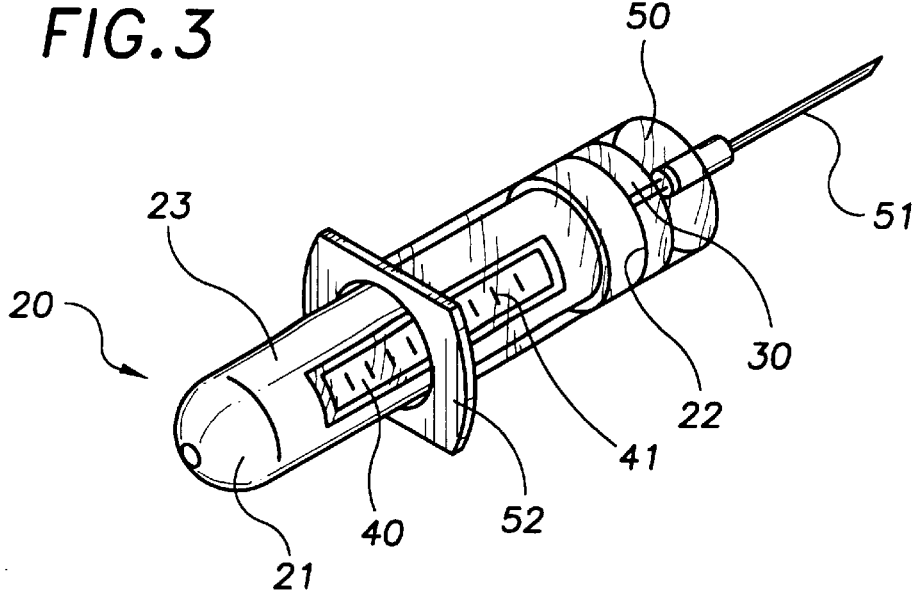

In operation, hollow tubular housing 20 is coupled to needle 51 via phlebotomy tube holder 50 wherein needle 51 punctures hermetic sealing member 30 as pressure is applied to flanges 52 of phlebotomy tube holder 50. Hollow tubular housing 20 should be maneuvered to place temperature sensitive level indicator 40 in an upright position for ease of visual inspection, as best seen in FIG. 3. Moreover, temperature sensitive level indicator 40 should be upright so that as the blood enters hollow tubular housing 20, temperature sensitive level indicator 40 is not immediately in contact with such blood. As the blood fills hollow tubular housing 20, the blood flows down a back side of elongated cylindrical member 23 and collects in rounded end 21. Thereafter, the blood level begins to rise along the front side of elongated cylindrical member 23. As the blood level increases, temperature sensitive level indicator 40 begins to change color when the blood reaches the area of temperature sensitive level indicator 40. As the blood level increases further, temperature sensitive level indicator 40 continues to change color wherein the plurality of graduated marker indicators 41 indicates the level of blood collected.

Although non-light penetrating phlebotomy tube 10 is useful in vacuum tube phlebotomy, the non-light penetrating properties and temperature sensitive level indicator are applicable to syringes which are capable of storing therein any fluid-type which may be sensitive to light exposure. Nevertheless, the non-light penetrating properties and temperature sensitive level indicator are advantageous for camouflaging the contents of a container while indicating the level of such contents.

It can be seen from the preceding description that a non-light penetrating phlebotomy tube 10 for protecting the collected blood stored therein from light exposure and for indicating the level of the blood being collected to prevent overdrawing and underdrawing has been provided.

It is noted that the embodiment of the non-light penetrating phlebotomy tube described herein in detail, for exemplary purposes, is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A non-light penetrating phlebotomy tube comprising:
    a non-light penetrating housing means for housing a fluid having an elongated cylindrical member wherein one distal end of said elongated cylindrical member is rounded and the other distal end of said elongated cylindrical member is open, the outer surfaces of said elongated cylindrical member being opaque;
    a hermetic sealing means received in said other distal end of said elongated cylindrical member for sealing the non-light penetrating housing means; and,
    a level detector means coupled to said elongated cylindrical member for detecting the level of a fluid entering said non-light penetrating housing means, said level detector means being a temperature sensitive level detector including a liquid crystal strip thermometer having a thermally sensitive strip having a plurality of graduated marker indicators.

2. The phlebotomy tube of claim 1, wherein said liquid crystal strip thermometer having a back surface provided with a self-adhesive material for adhering the liquid crystal strip thermometer to a longitudinal surface of said elongated cylindrical member.

* * * * *

UNITED STATES PATENT AND TRADEMARK OFFICE
CERTIFICATE OF CORRECTION

PATENT NO. : 5,900,291
DATED      : May 4, 1999
INVENTOR(S): Patricia J. Peebles It is certified that error appears in the above-identified patent and that said Letters Patent is hereby corrected as shown below:

On the title page:

Please change spelling of inventor's last name from (Pebbles) to --Peebles--

Signed and Sealed this

Seventeenth Day of April, 2001

NICHOLAS P. GODICI

Attest:

Attesting Officer    Acting Director of the United States Patent and Trademark Office